US005786349A

United States Patent [19]
Yamashita et al.

[11] Patent Number: 5,786,349
[45] Date of Patent: Jul. 28, 1998

[54] METHOD FOR TREATING CHLAMYDIA INFECTIOUS DISEASES BY RIFAMYCIN DERIVATIVE

[75] Inventors: Katsuji Yamashita, Kobe; Kazunori Hosoe, Takasago; Takayoshi Hidaka, Kobe, all of Japan; George Todaro, Seattle; Ribhi M. Shawar, Bellevue, both of Wash.

[73] Assignee: Kaneka Corporation, Osaka, Japan

[21] Appl. No.: 762,501

[22] Filed: Dec. 9, 1996

[30] Foreign Application Priority Data

Dec. 8, 1995 [JP] Japan .................. 7-320882
Jan. 10, 1996 [JP] Japan .................. 8-002634

[51] Int. Cl.$^6$ .................. A61K 31/33; A61K 31/535
[52] U.S. Cl. .................. 514/183
[58] Field of Search .................. 514/183

[56] References Cited

U.S. PATENT DOCUMENTS

| | | | |
|---|---|---|---|
| 4,690,919 | 9/1987 | Yamane et al. | 514/183 |
| 4,983,602 | 1/1991 | Yamane et al. | 514/229.5 |

FOREIGN PATENT DOCUMENTS 0 366 914  5/1990  European Pat. Off. .

OTHER PUBLICATIONS

Kunin, "Antimicrobial Activity of Rifabutin", Clinical Infectious Diseases, 22 (Suppl. 1), S3–14 (1996).
Abstract 2.05, "The Third International Conference on the Macrolides, Azalides and Strepyogramins", Jan. 24–26, 1996.
Jones et al., "In Vitro Activity of Rifamycins Alone or in Combination with Other Antibiotics Against Chlamydia Trachomatis", Reviews of Infectious Diseases, vol. 5, No. Suppl. 3, Jul. 1983–Aug. 1983, USA, pp. S556–S562.
Becker, "Antitrachoma Activity of Rifamycin B and 8–0–Acetylrifamycin S", Nature, vol. 231, 14 May 1971, USA, pp. 115–116, XP000647315.
T. Yamane et al., "Synthesis and Biological Activity of 3'-Hydroxy-5'-aminobenzoxazinorifamycin Drivatives", Chemical and Pharmaceutical Bulletin, vol. 41, No. 1, 1993, Japan, pp. 148–155, XP000197109.

Treharne et al., "In Vitro Studies of *Chlamydia trachomatis* Susceptibility and Resistance to Rifampin and Rifabutin", Antimicrobial Agents and Chemotherapy, vol. 33, No. 8, Aug. 1989, pp. 1393–1394.

Blamire et al., Proc. Nat. Acad. Sci. 71 (70), pp. 2867–2871, Jul. 1974.

*Primary Examiner*—Phyllis G. Spivack
*Attorney, Agent, or Firm*—Armstrong, Westerman, Hattori, McLeland & Naughton

[57] ABSTRACT

A method for treatment of diseases caused by Chlamydia infection is disclosed comprising administering a rifamycin of the formula (I):

(I)

[chemical structure]

wherein $R^1$ is hydrogen atom or acetyl, and X is oxygen, sulfur or a group NR, in which R is hydrogen, an alkyl group having 1 to 7 carbon atoms or a group of the formula (II):

(II)

$$-(CH_2)_n CH \begin{pmatrix} O \\ O \end{pmatrix}$$

in which n is an integer of 1 to 3;
or a physiologically acceptable salt thereof.

14 Claims, No Drawings

METHOD FOR TREATING CHLAMYDIA INFECTIOUS DISEASES BY RIFAMYCIN DERIVATIVE

BACKGROUND OF THE INVENTION

The present invention relates to a treatment of diseases resulting from infection with Chlamydia. More particularly, the invention relates to a method for treating diseases caused by Chlamydia infection, such as trachoma, inclusion conjunctivitis, lymphogranuloma inguinale, non-gonorrheal urethritis, pasittacosis, atypical pneumonia and coronary disease in an animal or human subject, which comprises administering to the subject a rifamycin derivative or a physiologically acceptable salt thereof.

*Chlamydia trachomatis* and *Chlamydia psittaci* are known as the Chlamydia, and have been known as a pathogen of trachoma, inclusion conjunctivitis, lymphogranuloma inguinale, non-gonorrheal urethritis, pasittacosis, etc. Recently, *Chlamydia pneumoniae* was newly found as a pathogenic microorganism of atypical pneumonia, and it is being made clear that this organism is also a pathogen of coronary diseases. It is known that tetracycline antibiotics such as minocycline and macrolide antibiotics such as clarithromycin are effective as therapeutic agents for diseases caused by known Chlamydia. However, it is known that since the tetracycline antibiotics themselves have a property of forming a chelate with a metal, they disturb calcium metabolism and may cause adverse effects such as deposition of tetracycline onto teeth, bone growing point disorder and induction of struma when applied to infants. It is also known that the macrolide antibiotics may cause adverse effects such as hepatopathy and arrhythmia when applied to subjects of an advanced age. In order to overcome these problems and to develop a therapy more effective for patients, it is necessary to introduce a new therapeutic agent.

An object of the invention is to provide an effective treatment of diseases caused by Chlamydia infection.

This and the other objects of the present invention will become apparent from the description hereinafter.

SUMMARY OF THE INVENTION

In accordance with the present invention, there is provided a method for treating diseases caused by Chlamydia infection in an animal or human subject, which comprises administering to the subject an effective amount of a rifamycin derivative of the formula (I):

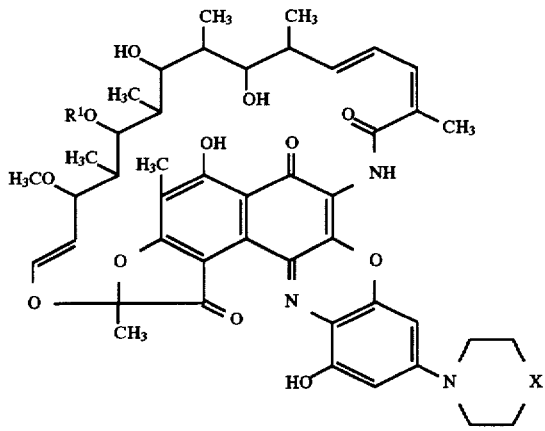

wherein $R^1$ is hydrogen atom or acetyl group, and X is oxygen atom, sulfur atom or a group NR in which R is hydrogen atom, an alkyl group having 1 to 7 carbon atoms or a group of the formula (II):

in which n is an integer of 1 to 3;
or a physiologically acceptable salt thereof.

DETAILED DESCRIPTION

In the rifamycin derivative (I) used in the present invention, X denotes an oxygen atom, a sulfur atom or a group NR wherein R is a hydrogen atom, an alkyl group having 1 to 7 carbon atoms or a group of the formula (II):

in which n is an integer of 1 to 3, and $R^1$ denotes a hydrogen atom or an acetyl group.

The alkyl group having 1 to 7 carbon atoms in R includes linear, branched and cyclic alkyl groups such as methyl group, ethyl group, propyl group, isopropyl group, cyclopropyl group, butyl group, isobutyl group, sec-butyl group, tert-butyl group, cyclobutyl group, cyclopropylmethyl group, pentyl group, isopentyl group, sec-pentyl group, tert-pentyl group, 1, 2-dimethylpropyl group, 1-ethylpropyl group, cyclopentyl group, cyclobutylmethyl group, hexyl group, 4-methylpentyl group cyclohexyl group, 3-methylcyclopentyl group, heptyl group, isoheptyl group, and the like. Methyl, ethyl, propyl, isopropyl and isobutyl groups are preferred.

A group of the formula (II'):

is preferred as the group shown by the formula (II).

Preferable combinations of the above-mentioned X and $R^1$ are shown in Table 1.

TABLE 1

| | X | $R^1$ |
|---|---|---|
| (a) | O | $COCH_3$ |
| (b) | NR (R = $C_1$ to $C_7$ alkyl group) | H |
| (c) | NR (R = $C_1$ to $C_7$ alkyl group) | $COCH_3$ |
| (d) | NR(R = —$(CH_2)_nCH\underset{O}{\overset{O}{\diagup\!\!\!\diagdown}}$ ) wherein n is an integer of 1 to 3) | $COCH_3$ |

The rifamycin derivative (I) used in the present invention for treating diseases caused by Chlamydia infection can be obtained by methods disclosed in, for example, Japanese Patent Publication Kokoku No. 5-57275, Japanese Patent Publication Kokai Nos. 3-007291, 3-101681 and 4-103589, and Chem. Pharm. Bull., Vol. 41, 148(1993).

The rifamycin derivative (I) is able to form a salt with either an acid or a base. As the acid or base which can be used for the salt formation, any one capable of forming a salt with the rifamycin derivative (I) can be used. Examples of the salt with a base are (1) metal salts, particularly alkali metal salts and alkaline earth metal salts, (2) ammonium salts, and (3) amine salts, particularly salts with methyl amine, ethyl amine, diethylamine, triethylamine, pyrrolidine, morpholine or hexamethyleneimine, and the like. Examples of the salt with an acid are (1) salts with mineral acids such as sulfuric acid and hydrochloric acid, and (2) salts with organic acids such as p-toluenesulfonic acid, trifluoroacetic acid and acetic acid.

A physiologically acceptable salt of the rifamycin derivative which can be used as a therapeutic agent for diseases caused by Chlamydia infection according to the present invention is selected from the above-mentioned salts.

The therapeutic agent for diseases caused by Chlamydia infection which contains as an effective component the rifamycin derivative (I), or its physiologically acceptable salt, according to the present invention may be, for example, in the form of an injection preparation such as an aqueous suspension injection preparation, an oil suspension injection preparation or an emulsion injection preparation. The solvent for the injection according to the present invention includes water, a water-miscible solvent and an oil solvent. Examples of the water-miscible solvent are ethanol, propylene glycol, polyethylene glycol, glycerol and other solvents miscible with water in any proportion. As the oil solvent, any in the form of liquid at ordinary temperature, such as vegetable oils and fatty acid esters, can be used. Examples of the vegetable oil are purified olive oil, peanut oil, sesame oil, camellia oil, and the like. The proportion of the agent for treating Chlamydia infectious diseases (effective component) in the injection preparations can be varied within the range of 0.2 to 50% by weight. Intradermic injection, hypodermic injection, intramuscular injection, intraperitoneal injection and the like can be used as the mode of administration of the injection preparations.

The therapeutic agent for diseases caused by Chlamydia infection which contains as an effective component the rifamycin derivative (I), or its physiologically acceptable salt, according to the present invention may also be in the form of preparations for oral administration such as powder, tablets, capsules, sugar-coated tablets, granules, syrups and the like. Carriers used for the preparations of the therapeutic agent for Chlamydia infectious diseases according to the present invention are organic or inorganic, solid or liquid, usually inactive pharmaceutical carriers suitable for oral administration. Examples of the carrier are, for instance, crystalline cellulose, gelatin, lactose, starch, magnesium stearate, talc, vegetable and animal oils and fats, gums, polyalkylene glycols, and the like. The amount of the therapeutic agent for Chlamydia infectious diseases (effective component) used in the present invention in the preparations can be varied within the range of 0.2 to 100 % by weight based on the carrier. The therapeutic agent for Chlamydia infectious diseases used in the present invention may include one or more other therapeutic agents for Chlamydia infectious diseases and/or other medicaments, which are compatible therewith. In that case, needless to say, the compound (I) or its salt does not have to be the main component in the preparations.

The therapeutic agent for Chlamydia infectious diseases used in the present invention is generally administered in such a dosage as to achieve the desired actions without any side effect. Although the actual dosage should be determined according to the judgement of doctors, the usual dosage of the compound (I) or its salt is from about 10 mg to about 10 g, preferably about 20 mg to about 5 g, per day for adults.

The compound (I) or its salt can be used in a pharmaceutical dosage unit containing it as the effective component in an amount of 1 mg to 5 g, preferably 3 mg to 1 g.

The therapeutic agent according to the invention is effective in treating diseases caused by Chlamydia infection in human being and animals such as warm-blooded animals.

The present invention is more specifically described and explained by means of the following Examples, but it is to be understood that the present invention is not limited to these Examples.

EXAMPLE 1

In 800 g of a purified sesame oil was suspended 200 g of compound 2 shown in Table 2 (a compound used in the present invention represented by the formula (I) wherein $X=NR=NCH_3$ and $R^1$ is $COCH_3$) which was aseptically prepared and pulverized into fine powder. The suspension was filled in brown ampoules in an amount of 2 g, and the ampoules were sealed to give oil suspension injection preparation containing 200 mg of compound 2 per gram.

EXAMPLE 2

In 800 g of a purified sesame oil was suspended 200 g of compound 4 shown in Table 2 (a compound used in the present invention represented by the formula (I) wherein $X=NR=NCH_2CH(CH_3)_2$ and $R^1$ is $COCH_3$) which was aseptically prepared and pulverized into fine powder. The suspension was filled in brown ampoules in an amount of 2 g, and the ampoules were sealed to give oil suspension injection preparation containing 200 mg of compound 4 per gram.

EXAMPLE 3

A mixture of 100 g of compound 2, 55 g of lactose and 41 g of a dried potato starch was kneaded with 20 ml of water, and was granulated by extruding through a 16 mesh screen and drying at 40° C. The obtained granules were uniformly mixed with 4 g of magnesium stearate, and the resulting mixture was tableted in a conventional manner to give tablets containing 100 mg of compound 2 per tablet weighing 200 mg.

EXAMPLE 4

A mixture of 100 g of compound 4, 55 g of lactose and 41 g of a dried potato starch was kneaded with 20 ml of water, and was granulated by extruding through a 16 mesh screen and drying at 40° C . The obtained granules were uniformly mixed with 4 g of magnesium stearate, and the resulting mixture was tableted in a conventional manner to give tablets containing 100 mg of compound 4 per tablet weighing 200 mg.

EXAMPLE 5

A mixture of 100 g of compound 5 shown in Table 2 (a compound used in the present invention represented by the formula (I) wherein $X=NR=NCH_2CH(CH_3)_2$ and $R^1$ is H), 55 g of lactose and 41 g of a dried potato starch was kneaded with 20 ml of water, and was granulated by extruding through a 16 mesh screen and drying at 40° C. The obtained granules were uniformly mixed with 4 g of magnesium stearate, and the resulting mixture was tableted in a conventional manner to give tablets containing 100 mg of compound 5 per tablet weighing 200 mg.

EXAMPLE 6

196 g of granules obtained in the same manner as in Example 3 and 4 g of magnesium stearate were mixed, and 200 mg portions of the resulting mixture were filled in No. 2 capsules to give hard capsules containing 100 mg of compound 2 per capsule.

EXAMPLE 7

196 g of granules obtained in the same manner as in Example 4 and 4 g of magnesium stearate were mixed, and 200 mg portions of the resulting mixture were filled in No. 2 capsules to give hard capsules containing 100 mg of compound 4 per capsule.

EXAMPLE 8

10.0 g of compound 2, 84.0 g of lactose, 4.5 g of crystalline cellulose and 1.5 g of magnesium stearate were thoroughly mixed to give a powder containing 100 mg of compound 2 per gram.

EXAMPLE 9

10.0 g of compound 4, 84.0 g of lactose, 4.5 g of crystalline cellulose and 1.5 g of magnesium stearate were thoroughly mixed to give a powder containing 100 mg of compound 4 per gram.

EXAMPLE 10

10.0 g of compound 5, 84.0 g of lactose, 4.5 g of crystalline cellulose and 1.5 g of magnesium stearate were thoroughly mixed to give a powder containing 100 mg of compound 5 per gram.

EXAMPLE 11

The strong antibacterial activity of the rifamycin derivative (I) against Chlamydia was demonstrated by in vitro tests 1 to 3 and a test of treating infected mice. (1) In vitro test 1.

The strong antibacterial activity of the rifamycin derivative (I) against Chlamydia was demonstrated by the effect of the rifamycin derivative against inclusion formation by Chlamydia in a test using cultured cells.

The antibacterial activity of a rifamycin derivative of the formula (I) wherein $X=NR=NCH_2CH(CH_3)_2$ and $R^1$ is $COCH_3$, namely acetyl group, (compound 4 shown in Table 2) was measured in vitro as follows:

According to the standard method provided in Japan Society of Chemotherapy [Chemotherapy, Vol. 40, 303 (1992)], HeLa 229 cells inoculated with a test Chlamydia were cultured at 37° C. for 3 days in Eagle's minimum essential medium containing 8% of a heat inactivated fetal calf serum in the presence of the test compound, and the minimum inhibitory concentration (MIC) capable of inhibiting inclusion formation was determined.

In the test using Chlamydia trachomatis F/UW-6/Cx and D/UW-3/Cx as the test Chlamydia with inoculation of $10^4$ inclusion-forming units, the MIC value of the compound 4 was 0.000125 μg/ml with respect to both strains, so it was found that the growth of Chlamydia can be inhibited at a very low concentration. The MIC value of the known agent rifampicin tested as a control agent under the same condition was 0.004 μg/ml with respect to the both strains. It is as high as about 30 times the concentration for the compound 4. These results show that the compound 4 according to the present invention is effective at a very low concentration as compared with the known agent. (2) In vitro test 2

The antibacterial activity of the compound 4 was estimated in vitro using other Chlamydia strains as follows:

According to the method of C. Kuo et al disclosed in Antimicrobial Agents and Chemotherapy, Vol. 32, 257 (1988), HeLa 229 cells inoculated with a test Chlamydia were cultured at 35° C. for 3 days in Eagle's minimum essential medium containing 10% of a fetal calf serum in the presence of the test compound, and the minimum a inhibitory concentration (MIC) capable of inhibiting inclusion formation was determined.

Chlamydia pneumoniae TW-183 and Chlamydia trachomatis B/TW-5/TO were used as the test Chlamydia, and $0.6 \times 10^4$ to $1.2 \times 10^4$ inclusion-forming units of each of these strains were inoculated. The test was repeated 3 times. The MIC values of the compound 4 were from 0.000125 to 0.00025 μg/ml with respect to the both strains, so it was found that the growth of Chlamydia can be inhibited at a very low concentration.

(3) In vitro test 3

*Chlamydia pneumoniae* TW-183 and *Chlamydia pneumoniae* AR-39 were used as the test Chlamydia, and $3.0 \times 10^4$ to $4.0 \times 10^4$ inclusion-forming units of the TW-183 strain and $2.3 \times 10^4$ to $5.3 \times 10^4$ inclusion-forming units of the AR-39 strain were inoculated, respectively. That is to say, the Chlamydia was inoculated in an amount of about 5 times the amount used in the in vitro test 2, and the test was repeated 2 or 3 times in the same manner as the test 2. The highest concentration of the MIC values obtained in two or three tests was determined as the MIC value for its compound, provided that the MIC value of a control agent, azithromycin, is the result obtained by one test procedure. The results are shown in Table 2.

TABLE 2

| Compound | X | $R^1$ | Minimum inhibitory concentration (μg/ml) | |
|---|---|---|---|---|
| | | | TW-183 | AR-39 |
| 1 | O | $COCH_3$ | 0.00063 | 0.00125 |
| 2 | $NCH_3$ | COCH3 | 0.00063 | 0.00016 |
| 3 | $NCH_2CH_2CH_3$ | $COCH_3$ | 0.005 | 0.00125 |
| 4 | $NCH_2CH(CH_3)_2$ | $COCH_3$ | 0.00125 | 0.00125 |
| 5 | $NCH_2CH(CH_3)_2$ | H | 0.00125 | 0.0025 |
| 6 | 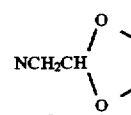 | $COCH_3$ | 0.0025 | 0.00063 |
| Azithromycin (control agent) | | | 0.25 | 0.5 |

*The compound number in the description corresponds to the compound number shown in Table 2.

It is known that the MIC values against Chlamydia pneumoniae TW-183 measured by the standard method of Japan Society of Chemotherapy [Chemotherapy, Vol. 40, 303(1992)] which is approximately the same as the method of the in vitro test 2, are from 0.016 to 0.031 μg/ml for minocycline and from 0.008 to 0.031 μg/ml for clarithromycin, which are considered to be the most effective among the known agents. With respect to results tested against Chlamydia trachomatis D/UW-3/Cx and Chlamydia psittaci Budgerigar No. 1, it is also known that the MIC value of minocycline is from 0.016 to 0.063 μg/ml for both strains, and the MIC value of clarithromycin is from 0.008 to 0.031 μg/ml for the both strains.

As shown in Table 2, it is apparent also from comparison with azithromycin tested as a control agent that the rifamycin derivatives used in the present invention exhibit a very strong antibacterial activity too in the in vitro test 3 wherein Chlamydia is inoculated in an amount of about 5 times that in the in vitro test 2.

7

In case of Chlamydia, it is known that the difference in susceptibility to antibacterial substances is small between different species and between different strains. The antibacterial activity of the rifamycin derivatives according to the present invention in which the MIC value is very small as compared with known agents indicates that the compounds according to the present invention would provide an excellent therapeutic agent for Chlamydia infectious diseases.

(4) Infection-therapy test

Using Swiss-Webster mice 4 weeks old, pneumonia models were prepared by inoculating $10^8$ inclusion-forming units of Chlamydia pneumoniae AR-39, per mouse, to the nose of mice, and the test was carried out using these models.

From two days after the infection, compound 4 shown in Table 2 was administered intraperitoneally 1 mg/kg/day to a treatment group of the mice continuously for 3 days, and a physiological saline was administered in the same manner to a control group of the mice. The effect of the tested agent was determined by comparing both groups. Chlamydia was reisolated from the lung tissue to evaluate the effect of the agent.

In the test, 23 mice were used for the treatment group, and 24 mice were used for the control group. The reisolation of Chlamydia from the mouse lung was conducted using 3 to 6 mice.

The results are shown in Table 3. As for the control group of mice, the death of one mouse, two mice and two mice was observed, respectively, 2 days, 7 days and 9 days after the infection, but no death of the treatment group of mice was observed. As for the control group of mice, the reisolation of organisms was observed up to the 14th day after the infection, namely up to the day corresponding to the 10th day after the- completion of the treatment. In contrast, as for the treatment group of mice, the reisolation of organisms was observed on only one mouse in a group of 5 mice on the third day after the completion of the treatment, and no reisolation of organisms was observed after the 5th day from the completion of the treatment.

From these results, it is understood that the death of mice caused by Chlamydia infection and the recovery of organisms are markedly inhibited by administration of the compound 4 according to the present invention.

TABLE 3

| Days after infection (Days after the completion of treatment) | Mice from which Chlamydia was reisolated from the lung/tested mice | |
|---|---|---|
| | Treatment group | Control group (Number of dead mice) |
| 2 (–) | 3/3 | 3/3 (1) |
| 7 (3) | 1/5 | 5/5 (2) |
| 9 (5) | 0/5 | 5/5 (2) |
| 14 (10) | 0/5 | 2/4* |
| 19 (15) | 0/5 | 0/6 |

*One of a group of 5 mice was excluded since bacterial contamination was observed upon detection of Chlamydia.

The rifamycin derivatives shown in Table 2 were orally administered to mice in a dose of 1,000 mg/kg. They did not show any toxicity, so it was confirmed that the rifamycin derivatives shown by the formula (I) are low in toxicity.

What we claim is:

1. A method for treating diseases caused by Chlamydia infection in an animal or human subject, which comprises administering to the subject an effective amount of a rifamycin compound of the formula (I):

8

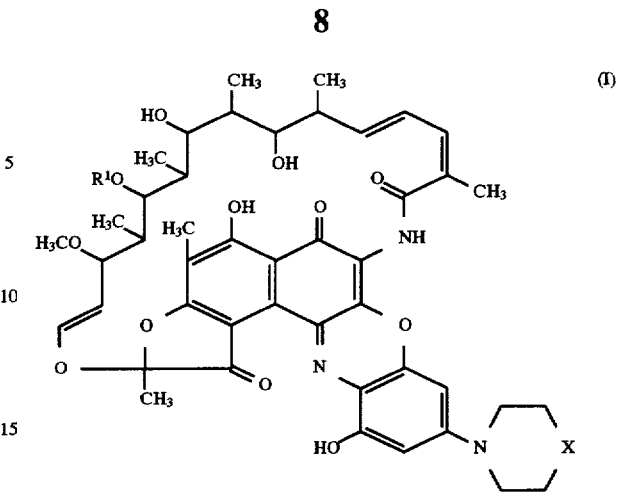

wherein $R^1$ is hydrogen atom or acetyl group, and X is oxygen atom, sulfur atom or a group NR in which R is hydrogen atom, a linear branched or cyclic alkyl group having 1 to 7 carbon atoms or a group of the formula (II):

in which n is an interger of 1 to 3 or a physiologically acceptable salt thereof.

2. The method of claim 1, wherein said R in said rifamycin compound (I) is a member selected from the group consisting of methyl group, ethyl group, propyl group, isopropyl group, cyclopropyl group, butyl group, isobutyl group, sec-butyl group, tert-butyl group, cyclobutyl group, cyclopropylmethyl group, pentyl group, isopentyl group, sec-pentyl group, tert-pentyl group, 1,2-dimethylpropyl group, 1-ethylpropyl group, cyclopentyl group, cyclobutylmethyl group, hexyl group, 4-methylpentyl group, cyclohexyl group, 3-methylcyclopentyl group, heptyl group and isoheptyl group.

3. The method of claim 1, wherein $R^1$ is an acetyl group and X is an oxygen atom; a group NR in which R is a linear branched or cyclic alkyl group having 1 to 7 carbon atoms; or a group NR in which R is a group of the formula (II):

in which n is an integer of 1 to 3.

4. The method of claim 1, wherein $R^1$ is a hydrogen atom and X is a group NR in which R is a linear branched or cyclic alkyl group having 1 to 7 carbon atoms.

5. The method of claim 1, wherein said salt is a salt with a base selected from the group consisting of an alkali metal, an alkaline earth metal, ammonium, methyl amine, ethyl amine, diethylamine, triethylamine, pyrrolidine, morpholine and hexamethyleneimine.

6. The method of claim 1, wherein said salt is a salt with an acid selected from the group consisting of sulfuric acid, hydrochloric acid, p-toluenesulfonic acid, trifluoroacetic acid and acetic acid.

7. The method of claim 1, wherein $R^1$ is an acetyl group and X is an oxygen atom;

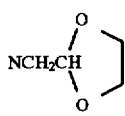

NCH$_3$; NCH$_2$CH$_2$CH$_3$; NCH$_2$CH(CH$_3$)$_2$; or

8. The method of claim 1, wherein R$^1$ is an acetyl group and X is NCH$_2$CH(CH$_3$)$_2$.

9. The method of claim 1, wherein said effective amount is from 10 mg to 10 g per day for adults.

10. The method of claim 1, wherein said Chlamydia is *Chlamydia pneumoniae* or *Chlamydia trachomatis*.

11. The method of claim 3, wherein said Chlamydia is *Chlamydia pneumoniae* or *Chlamydia trachomatis*.

12. The method of claim 4, wherein said Chlamydia is *Chlamydia pneumoniae* or *Chlamydia trachomatis*.

13. The method of claim 7, wherein said Chlamydia is *Chlamydia pneumoniae* or *Chlamydia trachomatis*.

14. The method of claim 8, wherein said Chlamydia is *Chlamydia pneumoniae* or *Chlamydia trachomatis*.

* * * * *